US011659979B2

(12) United States Patent
Garner

(10) Patent No.: US 11,659,979 B2
(45) Date of Patent: May 30, 2023

(54) CLAMP FOR A BRONCHOSCOPE OR THE LIKE

(71) Applicant: Justin Garner, Brentwood (GB)

(72) Inventor: Stefan Garner, Doddington (GB)

(73) Assignee: Justin Garner, Brentwood (GB)

( * ) Notice: Subject to any disclaimer, the term of this patent is extended or adjusted under 35 U.S.C. 154(b) by 0 days.

(21) Appl. No.: 17/778,755

(22) PCT Filed: Sep. 9, 2020

(86) PCT No.: PCT/EP2020/075206
§ 371 (c)(1),
(2) Date: May 20, 2022

(87) PCT Pub. No.: WO2021/099002
PCT Pub. Date: May 27, 2021

(65) Prior Publication Data
US 2023/0000334 A1    Jan. 5, 2023

(30) Foreign Application Priority Data

Nov. 22, 2019 (GB) ..................... 1917013

(51) Int. Cl.
*A61B 1/267* (2006.01)
*A61B 50/20* (2016.01)
(Continued)

(52) U.S. Cl.
CPC ........ *A61B 1/00148* (2022.02); *A61B 1/2676* (2013.01); *A61B 50/20* (2016.02);
(Continued)

(58) Field of Classification Search
CPC ... A61B 50/20; A61B 1/0014; A61B 1/00148; A61B 1/00147; A61B 1/2676;
(Continued)

(56) References Cited

U.S. PATENT DOCUMENTS 5,626,128 A * 5/1997 Bradley ............ A61M 16/0488
128/207.14
5,806,516 A    9/1998 Beattie
(Continued)

FOREIGN PATENT DOCUMENTS

CN   207186795 U   4/2018
CN   109663190 A   4/2019
(Continued)

OTHER PUBLICATIONS

International Search Report issued in PCT Application No. PCT/EP2020/075206, dated Sep. 12, 2020, pp. 4.
(Continued)

*Primary Examiner* — Marcela I. Shirsat
(74) *Attorney, Agent, or Firm* — Tutunjian & Bitetto, P.C.

(57) ABSTRACT

A clamp for inter alia a bronchoscope, the clamp comprising a spine with frame which has a channel through which a tube of inter alia the bronchoscope is received. The frame includes clamping means to grip the tube within the frame to fix it in position. The clamping is releasable to allow further movement of the tube relative to the frame.

13 Claims, 6 Drawing Sheets

(51) Int. Cl.
*A61M 25/02* (2006.01)
*A61M 16/04* (2006.01)
*A61B 1/00* (2006.01)

(52) U.S. Cl.
CPC ......... *A61M 25/02* (2013.01); *A61B 1/00147* (2013.01); *A61M 16/0488* (2013.01); *A61M 16/0497* (2013.01); *A61M 2025/024* (2013.01)

(58) Field of Classification Search
CPC .......... A61B 17/122; A61B 2050/0074; A61B 90/57; A61M 16/0497; A61M 16/04; A61M 16/0488; A61M 25/02; A61M 2025/022; A61M 2025/0213; A61M 2025/024
USPC ......................................................... 600/237
See application file for complete search history.

(56) References Cited

U.S. PATENT DOCUMENTS

| | | | |
|---|---|---|---|
| 9,522,043 | B1 | 12/2016 | Hoftman et al. |
| 2007/0135679 | A1* | 6/2007 | Hunt .................. A61B 1/00154 600/102 |
| 2007/0135770 | A1 | 6/2007 | Hunt et al. |
| 2007/0265497 | A1* | 11/2007 | Brown ................. A61B 1/0014 600/101 |

FOREIGN PATENT DOCUMENTS

| | | |
|---|---|---|
| WO | 20070130311 A2 | 11/2007 |
| WO | 2014025754 A1 | 2/2014 |
| WO | 20140183060 A2 | 11/2014 |

OTHER PUBLICATIONS

UK Search Report issued in UK Application No. GB1917013.3, dated May 19, 2020, pp. 2.

* cited by examiner

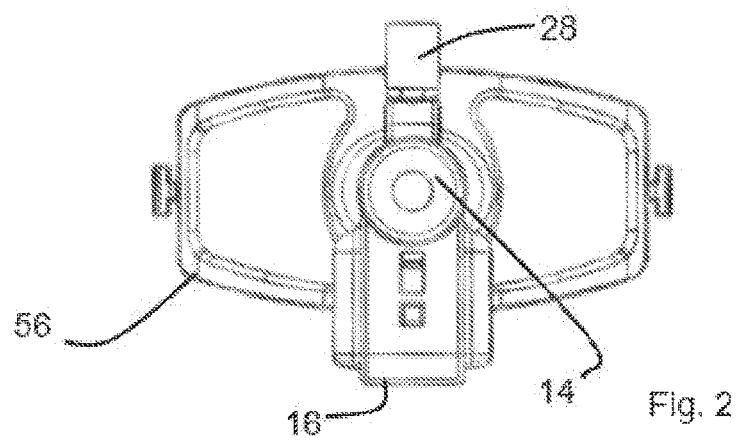
Fig. 2
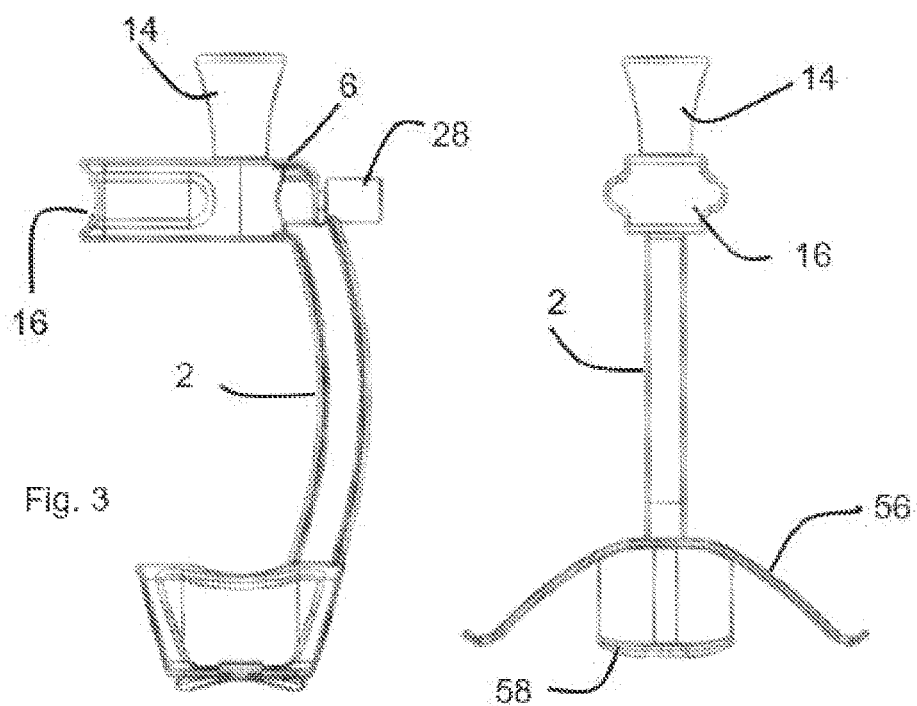
Fig. 3
Fig. 4

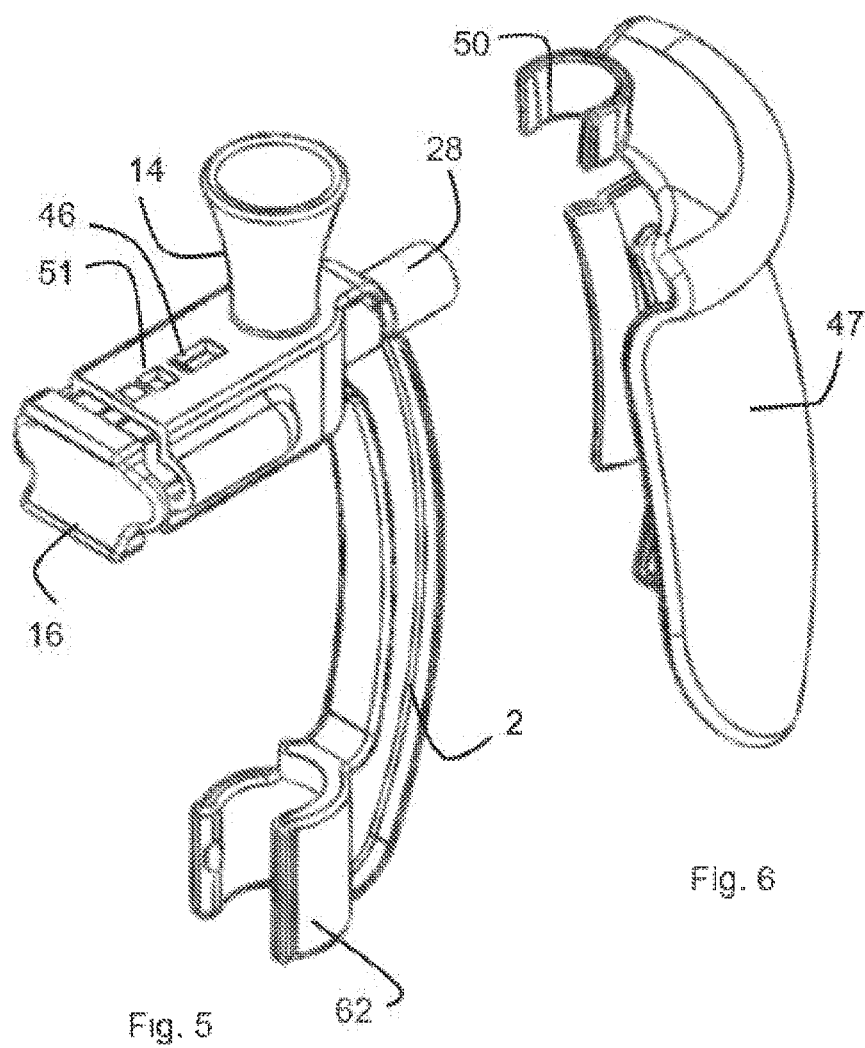

CLAMP FOR A BRONCHOSCOPE OR THE LIKE

FIELD OF INVENTION

The present invention relates to a clamp or grip for a bronchoscope, endoscope or the like. More specifically the invention relates to a re-settable clamp for a bronchoscopic tube to repeatedly fix and release the tube to facilitate repositioning and stabilisation during the medical procedure.

BACKGROUND TO THE INVENTION

Bronchoscopy is a procedure that allows a doctor to examine and operate in the upper airways, trachea, bronchi and smaller airways with a flexible multi-channel tube carrying a mini camera built into its tip. The tube is inserted into the airways, usually through the mouth, occasionally via the nose, a tracheostomy, or an endotracheal tube.

The doctor usually works with two assistants. One handles the bronchoscope passing it to the doctor who inserts and positions it in the patient's lung and who during the procedure repeatedly repositions it. This individual also assists the operator with transfer of instruments for diagnostic and therapeutic purposes via the working channel of the bronchoscope as well as the acquisition and preparation of samples where indicated. The second assistant secures the bronchoscope manually at the patient's mouth after each repositioning, in addition, keeping the patient's mouth clear of pooled secretions with a sucker, monitoring vital observations, and providing comfort and reassurance to the patient.

Dependence on trained staff is a necessity. In developing countries and increasingly a resource-starved British NHS it is a problem for personnel management.

The present invention seeks to provide a re-settable clamp which secures the bronchoscope in position at multiple sites selected by the doctor/operator, with the potential for reducing fatigue, repetitive strain, and dependence on assistants, and ultimately, ensuring patient safety.

STATEMENT OF INVENTION

According to a first aspect there is provided a clamp for inter alia a bronchoscope, the clamp comprising a spine having at one end a frame, the frame having a defined channel through which a tube of inter alia the bronchoscope is received, the frame further having clamping means to grip the tube within the frame to fix it in position, the clamping means being releasable to allow further movement of the tube relative to the frame.

Preferably, the frame extends substantially perpendicular to the spine at or near one end thereof.

Preferably, the connection between the spine and the frame defines the channel.

Preferably, an entrance of the channel is formed as a funnel to receive and direct the tube through the channel towards the distal end of the clamp.

Preferably, the frame has a hollow tubular structure to house a first clamping member, slidable within the frame.

Preferably, the distal end surface of the frame is formed as a push-button which is spring loaded to be depressed inwardly into the frame thereby to push the first clamping member further into the frame.

Preferably, the first clamping member is spring loaded and biased against the button.

Preferably, an outer surface of the button has an outwardly protruding projection extending beyond the dimensions of the frame to provide an abutment surface which abuts, in use, an end surface of the frame thereby to limit the depression distance of the button into the frame.

Preferably, the frame further houses a tubular sleeve member within the channel.

Preferably, the clamp further comprises an arm section extending perpendicularly from the spine opposite the frame, the arm section including a longitudinal internal channel through which extends a second clamping member the end of which abuts the respective side of the sleeve.

Preferably, the sleeve is formed with walls that are deformable to grip the tube when the sleeve is depressed from both sides by the first and second clamping members.

Preferably, the sleeve is made from silicone rubber.

Preferably, the distal end of the spine, has a mouthpiece adapter secured thereto.

Preferably, the distal end of the spine has an adapter for an endotracheal tube secured thereto.

Preferably, the clamp further comprising a hand grip removably attached to the clamp.

BRIEF DESCRIPTION OF THE DRAWINGS

Embodiments of the invention will now be described, by way of example only, with reference to the accompanying figures in which:

FIG. 2 is a plan view of the clamp of FIG. 1;

FIG. 3 is a side view of the clamp of FIG. 1;

FIG. 4 is a front view of the clamp of FIG. 1;

FIG. 5 is a perspective view of the clamp in an unclamped position, of a second embodiment to be used with an endotracheal tube (not figured);

FIG. 6 is a perspective view of a hand grip for connection to the clamp of FIG. 5;

DETAILED DESCRIPTION OF PREFERRED EMBODIMENTS

Figure 1:
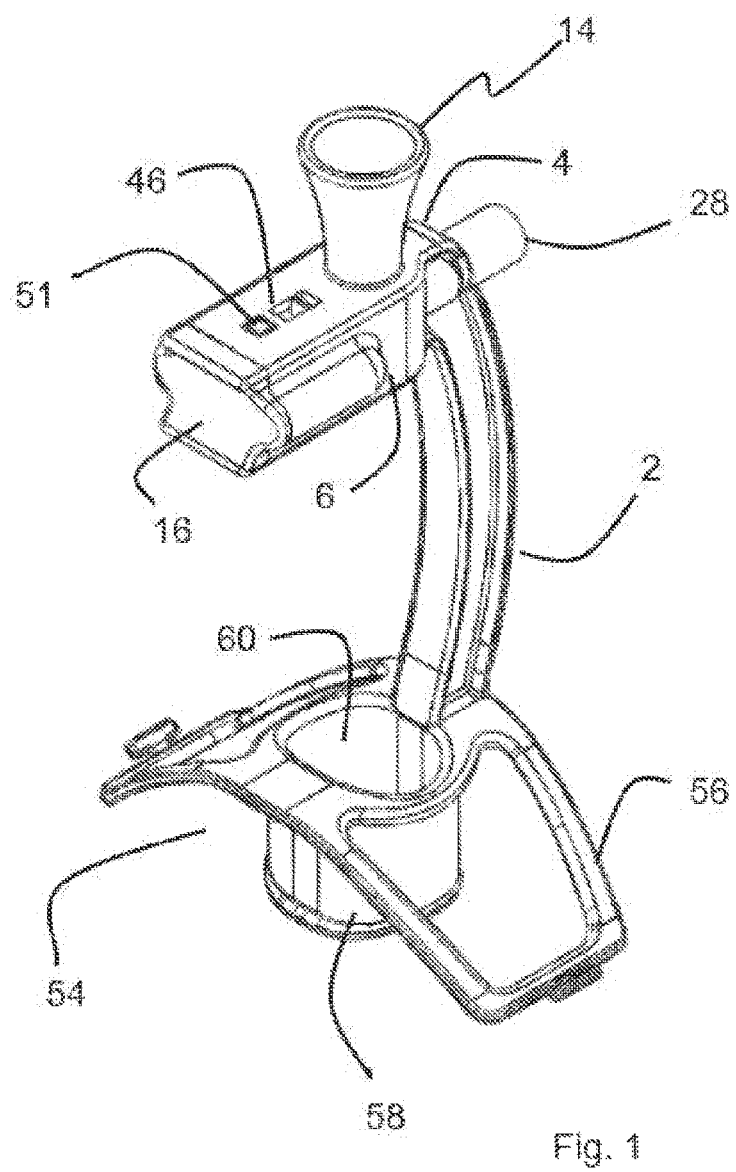
FIG. 1 is a perspective view of a clamp constructed in accordance with a first embodiment of the invention in a clamped position and incorporating a mouthpiece.
Figure 7:
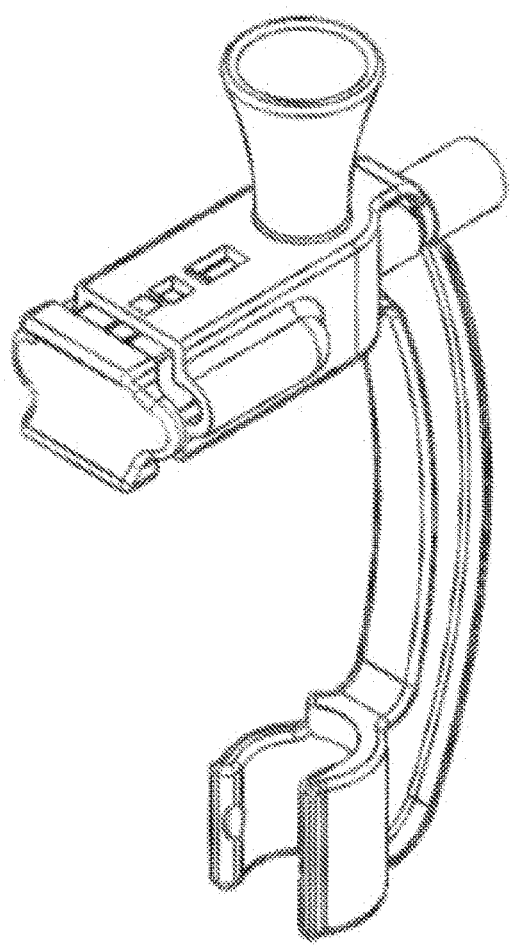
FIG. 7 illustrates the clamp with the hand grip connected.

Whilst the description refers to two embodiments, the main clamp structure and clamping mechanism is the same for both embodiments and the features of the invention described are applicable for the clamp shown in either FIG. 1 or FIG. 5.

Referring first to FIG. 1, the present invention provides a clamp for a bronchoscope tube. The clamp comprises a spine 2 which is orientated substantially vertically from the mouth of a supine patient during use.

The spine 2 has a generally C-shaped profile consisting of horizontally orientated end arms connected by a curve stem. The stem is curved for comfort and ease of use but may be straight.

One end (the top end 4 in use) has connected to it, a frame section 6 that extends generally horizontally from the end of spine 2, generally perpendicular to its stem.

Figure 8:
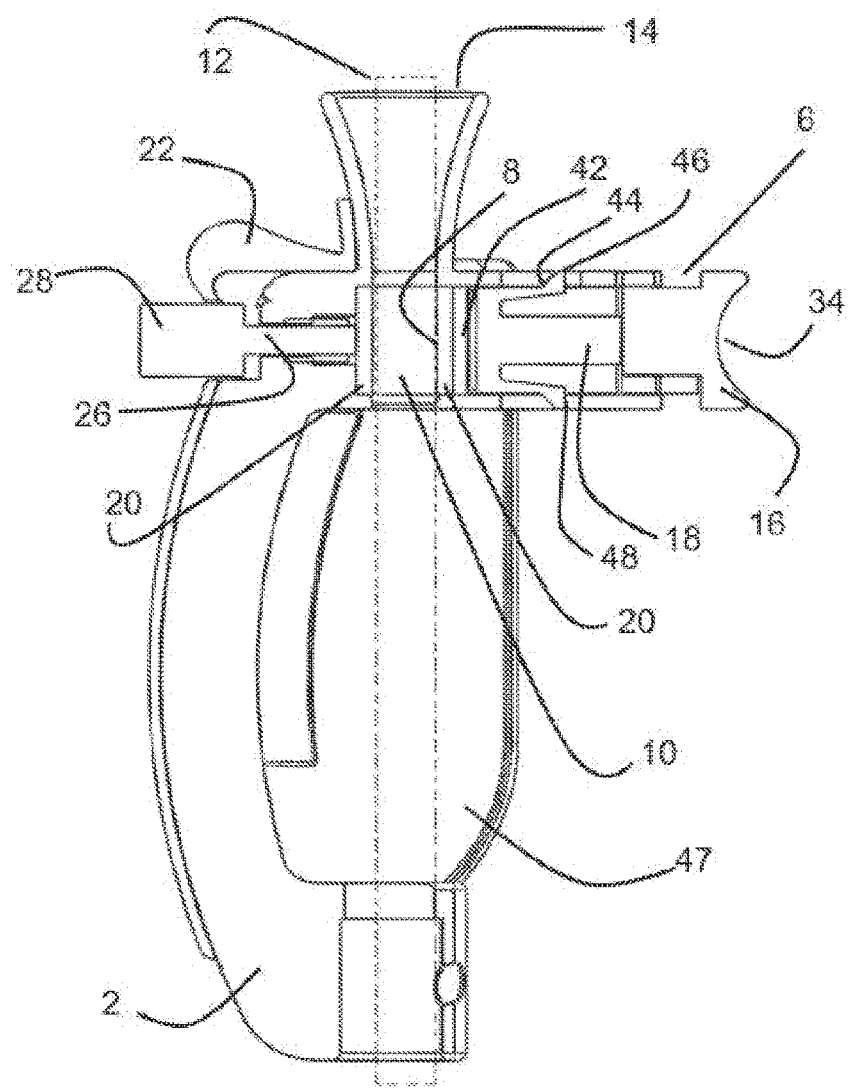
FIG. 8 is a cross-sectional view of the clamp of FIG. 7.

As can be seen best in FIG. 8, the connection between the end face of the spine 2 and the respective end 8 of the frame section 6 defines a vertical extending through-channel 10 via which a tube 12 of a bronchoscope is passed during use. The tube 12 is shown in dotted lines in FIG. 8. The entrance of the channel 10 is formed as a funnel 14 to receive and direct the tube 12 through the channel 10 to the base of the clamp and ultimately into the airway of a patient positioned below the clamp.

The frame section 6 and spine 2 may alternatively be formed integral with each other with the channel being defined by a through-aperture in the frame.

The distal end surface of the frame section 6 is formed as a push-button 16 to be depressed inwardly into the frame 6 by the user. As will be explained below with reference to FIGS. 8 and 9, depression of the button 16 causes the tube 12 to be gripped and retained in position at a desired height within the clamp.

The frame section 6 has a hollow tubular structure to house the clamping components. The components include, on one side of the tube 12, the push button 16 and a first clamping member 18 slidable within the frame housing 6.

Figure 9:
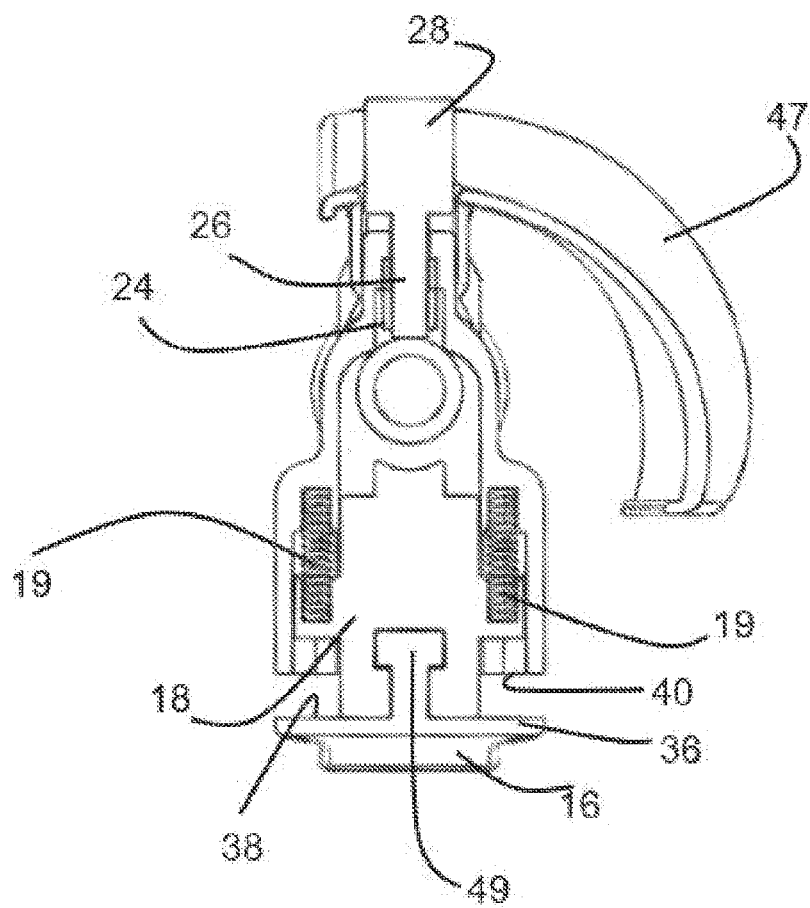
FIG. 9 is a plan view of the clamp of FIG. 7.

As can be seen in FIG. 9, the first clamping member 18 is spring loaded by having a coiled spring 19 on each side of the member 18 and is biased against the button 16. The springs 19 cause the button 16 to also be spring loaded.

As can be seen in FIG. 8, a tubular sleeve 20 made of silicone rubber or similar material is provided within the channel 10 through which the bronchoscopic tube 12 extends at the junction between the frame section 6 and the spine 2. The sleeve 20 forms the side walls of the channel 10 within the frame section 6. The walls of the sleeve 20 are deformable so as to grip the tube 12 when squeezed from one or both sides.

The horizontally aligned arm section 22 at the top of the spine 2 includes a longitudinal channel through which extends a second clamping member 26 the end of which abuts the respective side of the sleeve 20. The distal end of the second clamping member 26 has an integrally formed end cap 28.

The end cap 28 extends beyond the width of the second clamping member 26 such that it abuts against the outer wall of the arm section 22 of the spine 2 to limit the amount the second clamping member 26 can be depressed into the frame section 6, thereby to restrict the extent that the sleeve 20 can be deformed from that side in order to protect the tube 12.

The outer face of the button 16 has a curved depression 34 to receive and accommodate the thumb of the user to provide comfort to the user when depressing the button 16 which is likely to be required many times during the procedure. It can also be seen that the outer surface of the button 16 has an outwardly protruding projection 36 which extends beyond the dimensions of the frame 6. The projection 36 provides an abutment surface 38 which abuts, in use the end surface 40 of the frame 6 thereby to limit the depression distance of the button 16 into the housing 6 thereby to restrict the extent that the sleeve 20 can be deformed from that side in order to protect the tube 12.

Depression of the button 16 pushes the first clamping member 18 against the bias of the springs 19 into the frame section 6. Movement of the first clamping member 18 causes the end 42 of the clamping member 18 to abut and press against the channel sleeve 20 to deform the sleeve 20 slightly thereby to grip the tube 12, preventing any further vertical movement of the tube 12.

To cater for tubes 12 of varying diameter the distance the second clamping member 26 extends into the channel 24 can be delicately adjusted by rotation of the end cap 28.

The materials of the clamping components are carefully chosen to provide a delicate clamping mechanism to avoid any damage to the bronchosopic tube 12. Moreover, the grip of the tube 12 is such that it allows for rotation and manoeuvring of the tube 12 to vary the camera angle where necessary. The grip effectively acts as a gentle pivot point which allows for tube movement without affecting its height.

The first clamping member 18 includes a circumferential flange with projections 44 that come to project out of an aperture 46 of the frame section 6. The projections 44 have an abutment face 48 that abuts against the wall of the aperture 46 thereby locking the first clamping member 18 in position and preventing it from releasing but allowing further movement of the projection along the aperture towards the channel sleeve 20. The other surface of the projections 44 opposite the abutment face 48 is angled so to allow further insertion of the first clamping member 18 subject to its maximum insertion depth.

As can be seen in FIG. 9, the button 6 includes a T-shaped projection 49 that is received within a complimentary shaped recess in the first clamping member 18. The connection allows the button 16 to be moved in a vertical direction whilst still remaining engaged with the clamping member 18. The T-shaped projection 49 includes a locking tab (not shown) that extends through a further aperture 51 (FIGS. 1 and 5) in the frame section 6 when the button 16 is lifted by the thumb of an operator in order to lock the clamping member 18 in position.

The button 16 remains in such a position when the operator's thumb is removed from the button 16 and is only released when the operator pushes the button 16 downwardly to release the tab from the aperture 51.

The projections 44 and tab restrict the excursion of the first clamping member 18 preventing its ejection from the frame 6.

Whilst the first clamping member 18 is locked in position the tube 12 remains clamped in place, subject to its movement previously described. The clamp is reset when the operator fully releases the clamping member 18. This allows the tube 12 to be re-positioned for fixing at a different height.

FIG. 5 illustrates a hand grip 47 for connection to the clamp. The hand grip 47 is ergonomically designed to provide maximum comfort to both right-handed and left-handed users. The grip 47 has a smooth and sculptured surface. In an alternative embodiment, the surface of the grip may include a plurality of grooves to increase the grip.

The hand grip 47 is designed to be clipped on to the clamp by a push-fit mechanism to allow easy connection and disconnection. To this end the hand grip 48 has an arcuate structure to compliment the curvature of the stem of the spine 2 and has a U-shaped resilient clip connector 50 which, in use, clips around the base of the funnel 14 and a further U-shaped resilient clip connector that clips around spine 2.

Referring now back to FIG. 1, the base of the clamp connected to a mouthpiece adapter 54 to be placed in use, within the mouth of the patient such that the clamp extends upwardly from the supine patient's face.

The adapter 54 is of a form commonly used on medical apparatus and includes a face guard 56 section and a middle section 58 with a throughbore 60 providing a guiding channel within the patient's mouth through which the bronchoscopic tube 12 passes before entering the airways.

FIG. 5 illustrates the clamp of FIG. 1 with an endotracheal tube (ETT) adaptor 62 connected to the base of the spine 2. This permits connection to a double swivel elbow-joint with bronchoscopy port (not shown in the figures). This for example, allows the clamp to be suitable for use with patients under general anaesthetic.

The clamp herein before described provides an effective way to continually fix and release the bronchoscopic tube requiring little effort and movement of the doctor and little discomfort to the patient, thereby allowing the doctor greater flexibility to provide an effective bronchoscopy without assistance.

Whilst the embodiments described specifically relate to a bronchoscope, the clamp may have utility with any device that requires a re-settable clamping mechanism of a tube element.

The invention claimed is:

1. A clamp for inter alia a bronchoscope comprising: a spine having at one end a frame, the frame having a defined channel through which a tube of inter alia the bronchoscope is received, the frame further having clamping means to grip the tube within the frame to fix it in position, the clamping means being releasable to allow further movement of the tube relative to the frame wherein the frame has a hollow tubular structure to house a first clamping member of the clamping means, slidable within the frame and wherein the distal end surface of the frame is formed as a push-button which is spring loaded to be depressed inwardly into the frame thereby to push the first clamping member further into the frame.

2. The clamp according to claim 1, wherein the frame extends substantially perpendicular to the spine at or near one end thereof.

3. The clamp according to claim 2, wherein the connection between the spine and the frame defines the channel.

4. The clamp according to any one of claim 1, wherein an entrance of the defined channel is formed as a funnel to receive and direct the tube through the channel towards the distal end of the clamp.

5. The clamp according to claim 1, wherein the first clamping member is spring loaded and biased against the button.

6. The clamp according to claim 5, wherein an outer surface of the button has an outwardly protruding projection extending beyond the dimensions of the frame to provide an abutment surface which abuts, in use, an end surface of the frame thereby to limit the depression distance of the button into the frame.

7. The clamp according to any one of claim 1, wherein the frame further houses a tubular sleeve member within the defined channel.

8. The clamp according to claim 7, further comprising an arm section extending perpendicularly from the spine opposite the frame, the arm section including a longitudinal internal channel through which extends a second clamping member of the clamping means the end of which abuts the respective side of the tubular sleeve member.

9. The clamp according to claim 7, wherein the tubular sleeve member is formed with walls that are deformable to grip the tube when the tubular sleeve member is depressed from both sides by the first clamping member and a second clamping member of the clamping means.

10. The clamp according to claim 9, wherein the tubular sleeve member is made from silicone rubber.

11. The clamp according to claim 1, wherein the distal end of the spine, has a mouthpiece adapter secured thereto.

12. The clamp according to any one of claim 1, wherein the distal end of the spine has an adapter for an endotracheal tube secured thereto.

13. The clamp according to according to claim 1, further comprising a hand grip removably attached to the clamp.

* * * * *